United States Patent
Code et al.

(10) Patent No.: US 10,051,866 B2
(45) Date of Patent: Aug. 21, 2018

(54) ELECTROCHEMICAL DECONTAMINATION CELLS

(71) Applicant: BioLargo Life Technologies, Inc., Irvine, CA (US)

(72) Inventors: Kenneth R. Code, Edmonton (CA); Simmon Christian Hofstetter, Edmonton (CA); Ahmed Moustafa, Edmonton (CA); Alexander Evans, Edmonton (CA); Jenny Boutros, Edmonton (CA); Richard H. Smith, Edmonton (CA); Parastoo Pourrezaei, Edmonton (CA)

( * ) Notice: Subject to any disclaimer, the term of this patent is extended or adjusted under 35 U.S.C. 154(b) by 0 days.

(21) Appl. No.: 15/233,693

(22) Filed: Aug. 10, 2016

(65) Prior Publication Data

US 2017/0029298 A1 Feb. 2, 2017

Related U.S. Application Data

(63) Continuation-in-part of application No. 14/171,703, filed on Feb. 3, 2014, now abandoned, and a (Continued)

(51) Int. Cl.
*F02M 37/22* (2006.01)
*A01N 59/12* (2006.01)
(Continued)

(52) U.S. Cl.
CPC ........... *A01N 59/12* (2013.01); *C02F 1/283* (2013.01); *C02F 1/4672* (2013.01); *C02F 1/766* (2013.01); *C02F 2303/16* (2013.01)

(58) Field of Classification Search
CPC ... A61K 33/18; A61L 2/07; A61L 2/08; A61L 2/081; A61L 2/084; A61L 2/085; A61L 2/087; A61L 2209/00; A61L 2209/10; A61L 2209/11; A61L 9/00; A01N 25/02; A01N 25/08; A01N 25/22; A01N 2300/00; A01N 59/12; A01N 59/20
USPC ........... 204/228.3, 228.6, 230.2, 237; 210/170.01, 170.08, 195.1, 243, 532.2, 210/920, FOR. 103, FOR. 106; 422/22, 422/120
See application file for complete search history.

(56) References Cited

U.S. PATENT DOCUMENTS 4,800,011 A * 1/1989 Abbott ................. B01D 35/06
204/665
7,638,047 B1 * 12/2009 Jones ..................... C02F 1/288
210/252

(Continued)

*Primary Examiner* — Hayden Brewster
(74) *Attorney, Agent, or Firm* — Mark A Litman & Assoc. P.A.

(57) ABSTRACT

Contaminants are filtered from a fluid flow stream and the filter is regenerated by a process including steps of: providing a filter material comprising both carbon and potassium iodide; passing a contaminated fluid stream in contact with the filter material; adsorbing contaminants from the fluid stream onto surfaces in the filter material; passing an electric current through the filter material with adsorbed contaminant thereon; disassociating contaminant from the surfaces of the filter material; and removing disassociated contaminant from the filter material by carrying away the disassociated contaminant in a fluid flow mass.

17 Claims, 3 Drawing Sheets

Related U.S. Application Data continuation-in-part of application No. 13/475,102, filed on May 18, 2012, now Pat. No. 8,679,515, said application No. 13/843,615 is a continuation-in-part of application No. 13/843,615, filed on Mar. 15, 2013, now Pat. No. 8,846,067, and a continuation-in-part of application No. 12/009,586, filed on Jan. 18, 2008, now Pat. No. 8,226,964, said application No. 13/475, 102 is a continuation-in-part of application No. 12/009,586, filed on Jan. 18, 2008, now Pat. No. 8,226,964.

(60) Provisional application No. 61/490,448, filed on May 26, 2011.

(51) Int. Cl.
*C02F 1/28* (2006.01)
*C02F 1/467* (2006.01)
*A61L 9/00* (2006.01)
*C02F 1/76* (2006.01)

(56) References Cited

U.S. PATENT DOCUMENTS

2003/0196960 A1* 10/2003 Hughes .............. B01D 39/2068
                                                            210/670
2012/0263801 A1* 10/2012 Code .................... A01N 59/12
                                                            424/637

* cited by examiner

ELECTROCHEMICAL DECONTAMINATION CELLS

RELATED APPLICATIONS DATA

This application claims priority as a continuation-in-part of co-pending U.S. patent application Ser. No. 14/171,703 filed 3 Feb. 2014, titled "ANTIMICROBIAL SOLUTIONS AN METHODS" which is a continuation-in-part of U.S. patent application Ser. No. 13/843,615 filed 15 Mar. 2013, now U.S. Pat. No. 8,846,067 and a continuation-in-part of U.S. patent application Ser. No. 12/009,586 filed 18 Jan. 2008, now U.S. Pat. No. 8,226,964. This application also claims priority as a continuation-in-part of U.S. patent application Ser. No. 13/475,102, filed 18 May 2012, now U.S. Pat. No. 8,679,515 titled "Activated carbon associated with alkaline or alkali iodide" which is also a continuation-in-part of U.S. patent application Ser. No. 12/009,586 and claims the benefit of US Provisional Patent Application Ser. No. 61/490,448, filed 26 May 2011, titled "Activated carbon associated with alkaline or alkali iodide."

BACKGROUND OF THE INVENTION

1. Field of the Invention

The present invention relates to the field of carbon filters and slurries, particularly activated carbon filters and slurries and the regeneration of used or spent activated carbon after use as a filter, precipitator or biologic reactor. Concentrated and active stable solutions of iodine are also described.

2. Background of the Art

Activated carbon, also called activated charcoal or activated coal is a form of carbon that has been processed to make it extremely porous and thus to have a very large surface area available for adsorption or chemical reactions. The carbon may be provided by many different processes and in many of the various forms of carbon available, such as powdered carbon, expanded carbon, graphite, expanded graphite and the like.

The word activated in the name is sometimes replaced with active. Due to its high degree of microporosity, just 1 gram of activated carbon has a surface area in excess of 500 m.sup.2 (about one tenth the size of an American football field), as determined typically by nitrogen gas adsorption. Sufficient activation for useful applications may come solely from the high surface area, though further chemical treatment often enhances the adsorbing properties of the material. Activated carbon is usually derived from charcoal.

Activated carbon is carbon produced from carbonaceous source materials such as, by way of non-limiting examples, nutshells, peat, wood, coir, lignite, coal and petroleum pitch. It can be produced by one of the following non-limiting processes:

1. Physical reactivation: The precursor is developed into activated carbons using gases. This is generally done by using one or a combination of the following processes:

Carbonization: Material with carbon content is pyrolyzed at temperatures in the range 600-900° C., in absence of oxygen (usually in inert atmosphere with gases like argon or nitrogen)

Activation/Oxidation: Raw material or carbonized material is exposed to oxidizing atmospheres (carbon monoxide, oxygen, or steam) at temperatures above 250° C., usually in the temperature range of 600-1200° C.

2. Chemical activation: Prior to carbonization, the raw material is impregnated with certain chemicals. The chemical is typically an acid, strong base, or a salt (phosphoric acid, potassium hydroxide, sodium hydroxide, zinc chloride, respectively). Then, the raw material is carbonized at lower temperatures (450-900.degree. C.). It is believed that the carbonization/activation step proceeds simultaneously with the chemical activation. Chemical activation is preferred over physical activation owing to the lower temperatures and shorter time needed for activating material.

Activated carbons are complex products which are difficult to classify on the basis of their behavior, surface characteristics and preparation methods. However, some broad classification is made for general purpose based on their physical characteristics. They may be formally or informally characterized according to properties, method of production, morphology and/or other factors.

One form of activated carbon is known as powdered activated carbon (PAC). Activated charcoal under bright field illumination on a light microscope displays a fractal-like shape of the particles hinting at their enormous surface area. Each particle despite being only around 0.1 mm wide, has a surface area of several square meters.

Traditionally, active carbons are made in particulate form as powders or fine granules less than 1.0 mm in size with an average diameter between 0.15 and 0.25 mm. Thus they present a large surface to volume ratio with a small diffusion distance. PAC is made up of crushed or ground carbon particles, 95-100% of which will pass through a designated mesh sieve or sieve. Granular activated carbon is defined as the activated carbon being retained on a 50-mesh sieve (0.297 mm) and PAC material as finer material, while ASTM classifies particle sizes corresponding to an 80-mesh sieve (0.177 mm) and smaller as PAC. PAC is not commonly used in a dedicated vessel, owing to the high head loss that would occur. PAC is generally added directly to other process units, such as raw water intakes, rapid mix basins, clarifiers, and gravity filters.

Granular activated carbon is another form of activated carbon that has a relatively larger particle size compared to powdered activated carbon and consequently, presents a smaller external surface. Diffusion of the adsorbate is thus an important factor. These carbons are therefore preferred for all adsorption of gases and vapors as their rate of diffusion are faster. Granulated carbons are used for water treatment, deodorization and separation of components of flow system. GAC can be either in the granular form or extruded. GAC is designated by sizes such as 8×20, 20×40, or 8×30 for liquid phase applications and 4×6, 4×8 or 4×10 for vapor phase applications. A 20.times.40 carbon is made of particles that will pass through a U.S. Standard Mesh Size No. 20 sieve (0.84 mm) (generally specified as 85% passing) but be retained on a U.S. Standard Mesh Size No. 40 sieve (0.42 mm) (generally specified as 95% retained). AWWA (1992) B604 uses the 50-mesh sieve (0.297 mm) as the minimum GAC size. The most popular aqueous phase carbons are the 12.times.40 and 8.times.30 sizes because they have a good balance of size, surface area, and head loss characteristics.

Extruded activated carbon is another form that combines powdered activated carbon with a binder, which are fused together and extruded into a cylindrical shaped activated carbon block with diameters from 0.8 to 130 mm. These are mainly used for gas phase applications because of their low pressure drop, high mechanical strength and low dust content.

Impregnated carbon is a porous carbon containing several types of inorganic impregnant such as iodine (halogens and halogen ions), atomic, atomic aggregates, or nanoparticles of metal, silver, cations such as Al, Mn, Zn, Fe, Li, Ca have also been prepared for specific application in air pollution control especially in museums and galleries. Due to antimicrobial/antiseptic properties, silver loaded activated carbon is used as an adsorbent for purification of domestic water. Drinking water can be obtained from natural water by treating the natural water with a mixture of activated carbon and $Al(OH)_3$, a flocculating agent. Impregnated carbons are also used for the adsorption of $H_2S$ and thiols. Adsorption rates for $H_2S$ as high as 50% by weight have been reported.

Activated carbon is also available in special forms such as cloths and fibers. The "carbon cloth" for instance is used in personnel protection for the military.

A gram of activated carbon can have a surface area in excess of 500 $m^2$, with 1500 m.sup.2 being readily achievable. Carbon aerogels, while more expensive, have even higher surface areas, and are used in special applications.

Under an electron microscope, the high surface-area structures of activated carbon are revealed. Individual particles are intensely convoluted and display various kinds of porosity; there may be many areas where flat surfaces of graphite-like material run parallel to each other, separated by only a few nanometers or so. These micropores provide superb conditions for adsorption to occur, since adsorbing material can interact with many surfaces simultaneously. Tests of adsorption behavior are usually done with nitrogen gas at 77 K under high vacuum), but in everyday terms activated carbon is perfectly capable of producing the equivalent, by adsorption from its environment, liquid water from steam at 100° C. and a pressure of 1/10,000 of an atmosphere.

Physically, activated carbon binds materials by van der Waals force or London dispersion force. Activated carbon does not bind well to certain chemicals, including alcohols, glycols, strong acids and bases, metals and most inorganics, such as lithium, sodium, iron, lead, arsenic, fluorine, and boric acid. Activated carbon does adsorb iodine very well and in fact the iodine number, mg/g, (ASTM D28 Standard Method test) is used as an indication of total surface area. Ammonia adsorption on activated carbon is both temperature and concentration dependent, directly, in aqueous liquids.

Carbon monoxide is not well absorbed by activated carbon. This should be of particular concern to those using the material in filters for respirators, fume hoods or other gas control systems as the gas is undetectable to the human senses, toxic to metabolism and neurotoxic.

Activated carbon can be used as a substrate for the application of various chemicals which improve the adsorptive capacity for some inorganic (and problematic organic) compounds such as hydrogen sulfide ($H_2S$), ammonia ($NH_3$), formaldehyde (HCOH), radioisotopes iodine-$1^{31}$ and mercury (Hg). This property is known as chemisorption.

Iodine Number

Many carbons preferentially adsorb small molecules. Iodine number is the most fundamental parameter used to characterize activated carbon performance. It is a measure of activity level (higher number indicates higher degree of activation), often reported in mg/g (typical range 500-1200 mg/g). It is a measure of the micropore content of the activated carbon (0 to 20 Angstroms or up to 2 nm) by adsorption of iodine from solution. It is equivalent to surface area of carbon between 900 $m^2/g$ and 1100 $m^2/g$. It is the standard measure for liquid phase applications.

Iodine number is defined as the milligrams of iodine adsorbed by one gram of a material such as carbon, organic materials (such as oils, lipids, hydrocarbons, carbohydrates, etc.) when the iodine concentration in the residual filtrate is 0.02 normal. Basically, iodine number is a measure of the iodine adsorbed in the pores and, as such, is an indication of the pore volume available in the activated carbon of interest. Typically, water treatment carbons have iodine numbers ranging from 600 to 1100. Frequently, this parameter is used to determine the degree of exhaustion of a carbon in use. However, this practice should be viewed with caution as chemical interactions with the adsorbate may affect the iodine uptake giving false results. Thus, the use of iodine number as a measure of the degree of exhaustion of a carbon bed can only be recommended if it has been shown to be free of chemical interactions with adsorbates and if an experimental correlation between iodine number and the degree of exhaustion has been determined for the particular application. Although carbon is primarily described herein, any other surface on a material (porous or not) may also be used as long as it can sustain or provide an iodine number of at least 100 mg/g. Silicone materials, polymers, composites, coated substrates (such as carbon coated, or graphite coated substrates) and the like are examples thereof. These materials are preferably porous or microporous to allow high surface areas per volume of material.

Dechlorination

Some carbons are evaluated based on the dechlorination half-value length, which measures the chlorine-removal efficiency of activated carbon. The dechlorination half-value length is the depth of carbon required to reduce the chlorine level of a flowing stream from 5 ppm to 3.5 ppm. A lower half-value length indicates superior performance.

Ash Content

Ash content reduces the overall activity of activated carbon. It reduces the efficiency of reactivation. The metal oxides ($Fe_2O_3$) can leach out of activated carbon resulting in discoloration. Acid/water soluble ash content is more significant than total ash content.

Soluble ash content can be very important for aquarists, as ferric oxide can promote algal growths. A carbon with a low soluble ash content should be used for marine, freshwater fish and reef tanks to avoid heavy metal poisoning and excess plant/algal growth.

Carbon Tetrachloride Activity

Measurement of the porosity of an activated carbon by the adsorption of saturated carbon tetrachloride vapor.

Particle Size Distribution

The finer the particle size of an activated carbon, the better the access to the surface area and the faster the rate of adsorption kinetics. In vapor phase systems this needs to be considered against pressure drop, which will affect energy cost. Careful consideration of particle size distribution can provide significant operating benefits.

The most commonly encountered form of chemisorption in industry, occurs when a solid catalyst interacts with a gaseous feedstock, the reactant/s. The adsorption of reactant/s to the catalyst surface creates a chemical bond, altering the electron density around the reactant molecule and allowing it to undergo reactions that would not normally be available to it.

Carbon adsorption has numerous applications in removing pollutants from air or water streams both in the field and in industrial processes such as:

Spill cleanup.

Groundwater remediation

Drinking water filtration

Air purification

Volatile organic compounds capture from painting, dry cleaning, gasoline dispensing operations, and other processes.

Activated charcoal is also used for the measurement of radon concentration in air.

Activated carbon is also used as growth media in biologic methods of water and wastewater treatment.

SUMMARY OF THE INVENTION

A method and system generates reductive and/or oxidative chemical species in an aqueous fluid stream to disinfect and remove contamination by:

a) providing a filter material comprising at least one a porous carbon support layer and a silicate/glass wool layer;

b) passing an electric current through the filter material;

c) passing a fluid stream containing elemental halogens and/or halide salts through the filter material, distributing halogens or halides within the filter material;

d) directing a contaminated fluid mass into contact with the filter material in the presence of the electric current; and e) adsorbing contaminants from the fluid mass onto the filter material disinfecting or removing the contaminants.

DETAILED DESCRIPTION OF THE INVENTION

Figure 1:
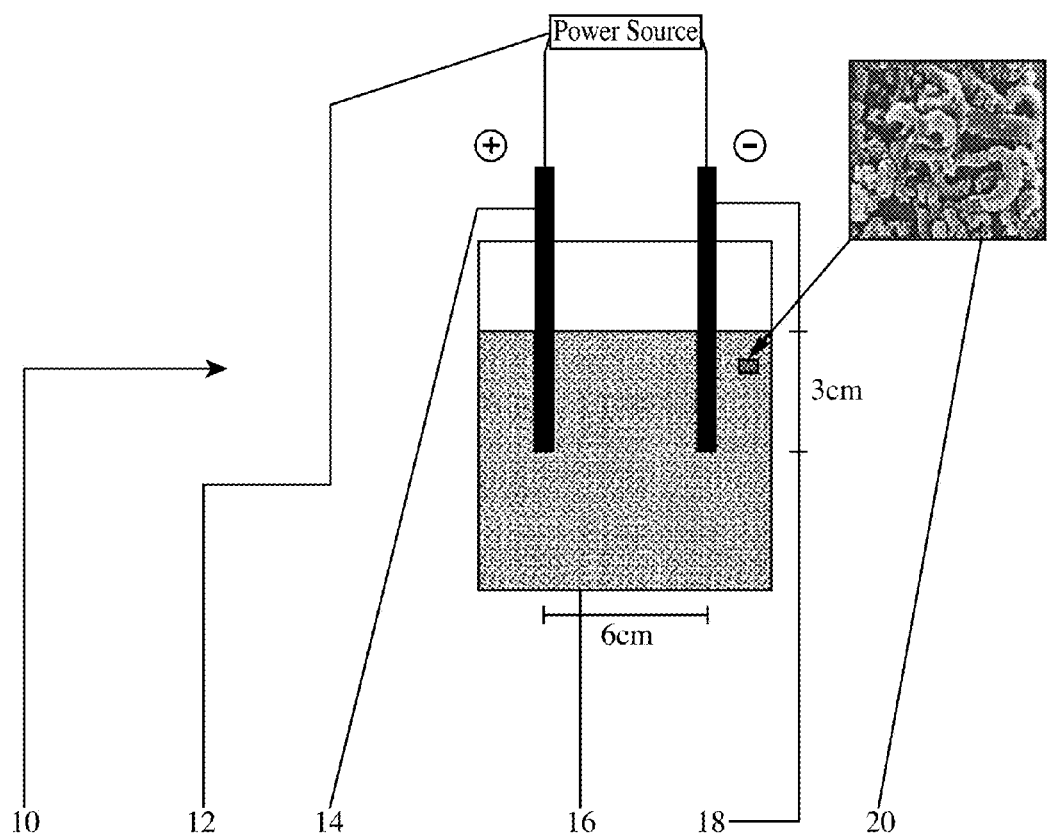
FIG. 1 is a schematic of an electrochemical batch cell according to at least one aspect of the present invention.

Research is being done testing various activated carbons' ability to store natural gas and hydrogen gas. The porous material acts like a sponge for different types of gasses. The gas is attracted to the carbon material via Van der Waals forces. Some carbons have been able to achieve bonding energies of 5-10 kJ per mol. The gas may then be desorbed when subjected to higher temperatures and either combusted to do work or in the case of hydrogen gas extracted for use in a hydrogen fuel cell. Gas storage in activated carbons is an appealing gas storage method because the gas can be stored in a low pressure, low mass, low volume environment that would be much more feasible than bulky on board compression tanks in vehicles.

Filters with activated carbon are usually used in compressed air and gas purification to remove oil vapors, odors, and other hydrocarbons from the air. The most common designs use a 1 stage or 2 stage filtration principle in which activated carbon is embedded inside the filter media. Activated charcoal is also used in spacesuit Primary Life Support Systems. Activated charcoal filters are used to retain radioactive gases from a nuclear boiling water reactor turbine condenser. The air vacuumed from the condenser contains traces of radioactive gases. The large charcoal beds adsorb these gases and retain them while they rapidly decay to non-radioactive solid species. The solids are trapped in the charcoal particles, while the filtered air passes through.

Activated carbon is commonly used to purify homemade non-dangerous chemicals such as sodium acetate. Activated carbon, often impregnated with iodine or sulfur, is widely used to trap mercury emissions from coal-fired power stations, medical incinerators, and from natural gas at the wellhead. This carbon is a specialty product costing more than US$4.00 per kg. However, it is often not recycled, if it can be.

The regeneration of activated carbons involves restoring the adsorptive capacity of saturated activated carbon by desorbing adsorbed contaminants on the activated carbon surface. This has been practiced with a number of available techniques. The most common regeneration technique employed in industrial processes is thermal regeneration. The thermal regeneration process generally follows three steps:

Adsorbent drying at approximately 105° C.

High temperature desorption and decomposition (500-900° C.) under an inert atmosphere Residual organic gasification by an oxidizing gas (steam or carbon dioxide) at elevated temperatures (800° C.)

The heat treatment stage utilizes the exothermic nature of adsorption and results in desorption, partial cracking and polymerization of the adsorbed organics. The final step aims to remove charred organic residue formed in the porous structure in the previous stage and re-expose the porous carbon structure regenerating its original surface characteristics. After treatment the adsorption column can be reused. Per adsorption-thermal regeneration cycle between 5-15 wt % of the carbon bed is burnt off resulting in a loss of adsorptive capacity. Thermal regeneration is a high energy process due to the high required temperatures making it both an energetically and commercially expensive process. Plants that rely on thermal regeneration of activated carbon have to be of a certain size before it is economically viable to have regeneration facilities onsite. As a result it is common for smaller waste treatment sites to ship their activated carbon cores to a specialized facility for regeneration, increasing the process' already significant carbon footprint http://www.prominentinc.com/cbac_impregnated_ki_nai.html discloses KI impregnated activated carbon.

KI/Potassium Iodide Impregnated Coal Based Activated Carbon.

It is effective for the desulphurization of gases and the removal of acidic contaminants such as hydrogen sulfide, hydrogen chloride, and mercaptans. The percentage of potassium iodine can be varied upon request.

The apparatus may be alternatively described as an apparatus for disinfection and removing contamination from a fluid including at least one cell:

a) a housing containing a filter material comprising at least one of porous carbon and silicate/glass wool;

b) a spacer material comprising silicate/glass wool, in contact with adjacent filter material, to separate filter material into discrete sections;

b) a fluid inlet port to the housing;

c) a fluid outlet port from the housing corresponding to each discrete section of filter material as separated by a spacer material;
d) a source of contaminated fluid mass available to the fluid inlet port;
e) a source of halide ions or elemental halogen in an aqueous carrier available for movement into the filter material;
f) a source of pressure for moving active fluid selected from the group consisting of the contaminated fluid mass and the halide ions or element halogen in an aqueous carrier through the inlet port and through the outlet port;
g) a current source configured to pass a voltage of between 0.05 and 36 volts across the filter material; and
h) a source of fluid flow mass to move fluid mass through the filter material during passage of direct current through the filter material.

Multiple cells can be provided, in parallel (preferred) or in series to increase the decontamination and volume flow through in the system. The power source is preferably direct current, although alternating current or pulsed current may be used. Multiple segments of the filter material separated by the spacer material can be included within the housing, such as three, for, five, six or seven filter layers separated by two, three, four, five and six spacer layers, respectively. The dimensions of the layers is based on the size of the unit and its desired flow-through capacity. Individual layers of at least 0.2 mm are functional, with layers of 10 cm each (or more, up to 50 cm) being more industrial size units.
Table Available Unit Products Range Remarks Mesh Size US GAC: 4× 6/ or as required Sieve 4× 8/4× 10/8× 20 Diameter mm PAC: 1.5/3.0/4.0 or as required Iodine mg/g Minimum 1000 or as required CCL4/CTC % Minimum 60/65/70/75 or as required KI Impregnation % Minimum 2/3/5 or as required $H_2S$ Break g/cc Minimum 0.14 or as required Through Capacity Apparent Density g/cc 0.50-0.66 or as required Hardness % Minimum 90/95 or as required Moisture % Maximum 15 or as required Chemical and Engineering News, Apr. 10, 2010, Volume 88, No. 6 "Wastewater Treatment," Melody Voith, discloses a process for cleaning wastewater from paper plant manufacturing sites by adsorption of organic chemical wastes by passing low-voltage electric current through a graphite-based filter to cause electrochemical oxidation of organic on the particles. The carbon particles are first mixed with the wastewater top absorb the organic wastes. The current directly oxidizes the organic materials.

carbon filter is activated by intimate, internal association with iodine and/or potassium iodide (KI). This material will be referred to herein as IAC (for Iodine (iodide) activated carbon. Spent or used IAC is saturated in an aqueous or alcoholic liquid while a current (e.g., DC or pulsed current) is passed through the spent IAC. The current both regenerates the IAC and oxidizes these contaminants. It regenerates the activity in the IAC by overcoming the forces binding the adsorbed materials to the IAC permitting the liquid supports to carry away the released formerly filtered and retained materials. As the adsorbed or absorbed materials filtered from either a gaseous or liquid medium are primarily associated with the activated carbon medium (the IAC) through electrical forces, as opposed to covalent bonding, application of current can be highly effective in freeing material bound to the IAC. The current also causes free iodine to be emitted from the KI and over the KI, and the iodine system oxidizes the adsorbed pollutants/contaminants. Rather than a direct electrochemical oxidation that must be tailored for each pollutant, the present system allows a single voltage to release the iodine which can then address any pollutant. The carbon may be reactivated, regenerated by adding additional KI into the carbon, as by passing a solution through the filter material, with adsorption of the KI molecules, with or without drying of the reactivating solution. In addition, the applied voltage and current may be optimized to yield only oxides as reaction products through reactions with autogenerated iodine pentoxides and other oxidative moieties, thus preserving the initial charge of iodide within the activated carbon. Additionally, a stable acidified iodine ($I_2$) solution is disclosed.

U.S. Pat. No. 7,850,764 (DeBerry) describes removal of contaminants from vapor streams and incidentally discloses regeneration of the filter media by heating the used activated carbon, especially to release bound mercury or by using a complexing agent to reduce or oxidize the bound mercury and make it available for removal.

U.S. Pat. No. 7,736,611 (Norberg) discloses filter materials that are regenerated by heating or vapor flushing, including activated carbon filters.

U.S. Pat. No. 7,442,352 (Lu) discloses uses for removing contaminants using activated carbon and regenerating the activated carbon by thermal degassing or washing out of the gases.

U.S. Pat. No. 6,953,494 (Nelson) teaches the use o bromine gas in activated carbon to improve its ability o adsorb mercury from combustion emission.

U.S. Pat. No. 6,638,347 (El-Shoubary) discloses carbon-based, adsorption powder containing an effective amount of cupric chloride suitable for removing mercury from a high temperature, high moisture gas stream, wherein the effective amount of cupric chloride ranges from about 1 to about 45 wt percent. Additional additives, such as potassium permanganate, calcium hydroxide, potassium iodide and sulfur, may be added to the powder to enhance the removal of mercury from the gas stream.

All references cited herein are incorporated by reference in their entireties.

Carbon filters and especially activated carbon filters are capable of removing contaminants from fluid media (aqueous or liquid media). Among the species of contaminants are selected from the group consisting essentially of basic, acidic and hydrocarbon species. Other contaminants may include metal, semimetals, and ionic species. Any material that can be temporarily adsorbed or adsorbed by activated carbon by electrical forces (including Van der Waals forces) should be capable of removal by treatment according to the technology described herein.

Electrochemical (EC) disinfection has been considered for water treatment since the 1950's. Systems that employ EC disinfection typically achieve microbial inactivation either by direct electrolysis or via generation of oxidants in situ, such as free chlorine, hydrogen peroxide, and other short-lived chemical species. Oxidant-generating EC systems that rely on chemicals already present in solution negate the need for transport and storage of chemicals such as chlorine. As an alternative to conventional water treatment, EC disinfection is inexpensive, poses little environmental hazard, has potential for automation, and has been shown to inactivate a wide variety of microorganisms, including viruses, bacteria, and algae (Bergmann et al., 2002). Halogens are of particular interest in EC disinfection because they can readily produce oxidants in an EC system. For example, chloride (NaCl) and bromide (NaBr) have been shown to be an effective source of oxidants (Stoner et al., 1982).

Chlorine has a history of use in water disinfection, although some microorganisms have been shown to exhibit resistance to chlorine (e.g., *Cryptosporidium parvum*). The use of chlorine as a disinfectant in solution can also lead to the formation of by-products of concern, some of which are carcinogenic or possibly teratogenic. The use of chlorine in EC disinfection is relatively popular and relies on generating oxidants via EC treatment of solutions containing low levels of chloride, such as seawater or brackish water (Patermarakis and Fountoukidis, 1990) (Butterfield et al., 1997). Chlorine in such EC systems has been shown to effectively inactivate both *C. parvum* oocysts and *Clostridium perfringens* spores (Bergmann et al., 2008) (Venczel et al., 1997). It should be noted that EC systems that use chlorine as an oxidant may also generate by-products of concern.

As with chlorine, iodine has a history of use as a disinfectant and antiseptic, although its potential for EC disinfection has not been thoroughly assessed. Disinfectant solutions containing iodine and iodide are numerous and among the oldest used. Most notable among these is Lugol's solution ($I_2$=155.6 ppm) (Gottardi, 2001), also known as Strong Iodine Solution (USP XXIII) Iodine has been used in veterinary medicine, human medicine, and to treat water since it is effective against bacteria, fungi, and viruses. In solution, iodine ($I_2$) and hypoiodous acid (HOI) are the predominant antimicrobial agents. Unlike chlorine, iodine in solution does not readily react with ammonia or other nitrogenous compounds, reacting with proteins up to three times slower than chlorine and four times slower than bromine, and does not form N-iodo compounds. Thus, in theory, in the presence of microorganisms in a complex solution, an iodine preparation may have additional time to enter cells and exact antimicrobial activity. Iodine's relatively slower reactivity, particularly with respect to protein, also allows for lower concentrations of iodine to be effective for disinfection. Compared to chlorine, iodine is also less likely to produce compounds that irritate or are odorous (e.g., U.S. Pat. No. 4,619,745).

Expanded graphite was added to the batch system as a means of increasing reactive surface area. Similar reasoning for electrode design has been used elsewhere (Stoner et al., 1982) (Tanaka et al., 2013). Graphite electrodes were used due to their low cost. *S. enterica* strains were chosen because of their role as an enteric pathogen.

2. Materials and Methods 2.1 Bacterial Cultures and Cocktail Preparation

Five *S. enterica* strains were obtained for use in a cocktail to challenge the efficacy of Cupridyne® solution in an EC batch cell. These strains are: *S. enterica* Typhimurium AAFRD 18, *S. enterica* AAFRD 49, *S. enterica* AAFRD 56, *S. enterica* AAFRD 58, and *S. enterica* AAFRD 59. All bacterial culture stocks were stored in 60% glycerol at −80° C. until needed.

A cocktail of *S. enterica* strains was prepared for each replicate tested in the EC batch system. For each cocktail, bacteria were aseptically streaked onto Violet Red Bile Agar (Difco™, Sparks, Md., USA) from −80° C. stocks and incubated at 37° C. for 24 hs. Following plate incubation, single colonies were picked and inoculated into 250 mL Trypticase Soy Broth (BBL™, Sparks, Md., USA) and incubated at 37° C. for 24 hs. Following broth incubation, equal parts of each *S. enterica* broth culture was mixed to produce cocktails as needed.

2.2 Preparation of Expanded Graphite and Cupridyne® Solutions/Iodine Solutions

A simple EC batch cell was made by placing expanded graphite in contact with graphite electrodes in a beaker. Expandable graphite was obtained from Asbury Carbons. Flake graphite was expanded by heating to 1000° C. in a muffle oven (Lindberg Blue M Box Furnace BF51700 Series, Thermo Fisher Scientific, USA) for 30 min.

All solution concentrations are given as parts per million iodine ($I_2$). Cupridyne® solutions were made by dissolving potassium iodide (KI; Sigma Aldrich) in sterile distilled water, followed by addition of copper sulfate ($CuSO_4 \cdot 5H_2O$; Sigma Aldrich). All Cupridyne® solution stoichiometry used in solution preparation is as follows:

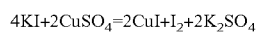

$$4KI + 2CuSO_4 = 2CuI + I_2 + 2K_2SO_4$$

Solutions were prepared immediately prior to addition to the EC batch ell. Solutions used contained 25, 50, 100, 250, and 500 ppm $I_2$.

2.3 Electrochemical (EC) Batch Running Parameters and Sampling

Cupridyne® solutions containing expanded graphite and a *S. enterica* cocktail were subjected to an electric field to assess whether this enhances bacterial inactivation. EC batch cells were made by placing a cocktail of *S. enterica* (100 mL) and a Cupridyne® solution (100 mL) into a beaker (500 mL) for a total volume of 200 mL. Batch cells with expanded graphite contained 1 g of the material. Graphite electrodes (12 cm length, spaced 6 cm apart center to center; FIG. 1) were partially submerged in solution (depth of 3 cm; FIG. 1). Samples were agitated using magnetic stir bars (450 rpm) such that the graphite did not form a stationary surface layer. Samples exposed to electricity were run at 24 V using a DC power supply (GQ Electronics DC Power Supply GQ-A305D, Seattle, Wash., USA). Amperage and pH, before and after treatment were recorded via the power supply and pH strips (Thermo Fisher Scientific, USA), respectively; samples were agitated prior to measuring pH. Temperatures were recorded before and after trials using an IR thermometer (Extech Instruments 42510A, Nashua, N.H., USA). Samples (1 mL) were extracted from running batches prior to treatment, and at 2.5, 5, 10, 15, 20, and 30 min. Samples were immediately plated onto VRBA using a spiral plater (Whitley Automated Spiral Plater, Shipley, West Yorkshire, UK), the surface of the plates allowed to dry, and incubated at 37° C. for 24 hours. It should be noted that samples were also plated on TSA to discern extent of sub-lethal injury to bacterial cells; no difference was noted between counts obtained from VRBG and TSA (data not shown) and plating on TSA was discontinued after initial trials.

3.1 Inactivation of *S. enterica*.

Figure 2A:
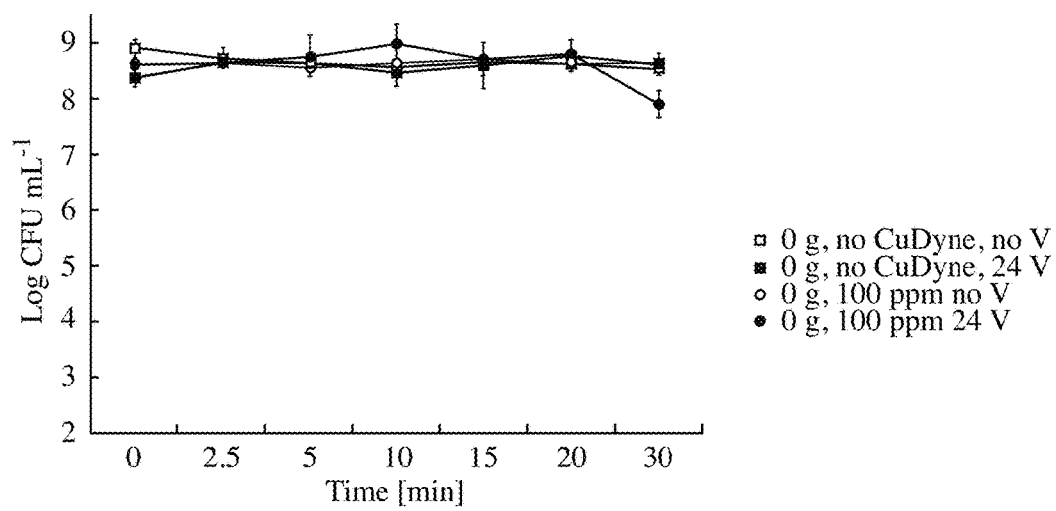
FIG. 2A is a graphic representation of Electrochemical treatment of *Salmonella enterica* cocktail in the absence of expanded graphite (2a: □0 g, no CuDyne, no V; ■0 g, no CuDyne, 24 V; ○0 g, 100 ppm, no V; ●0 g, 100 ppm, 24 V) and presence of expanded graphite (2b: □1 g, no CuDyne, no V.
Figure 2B:
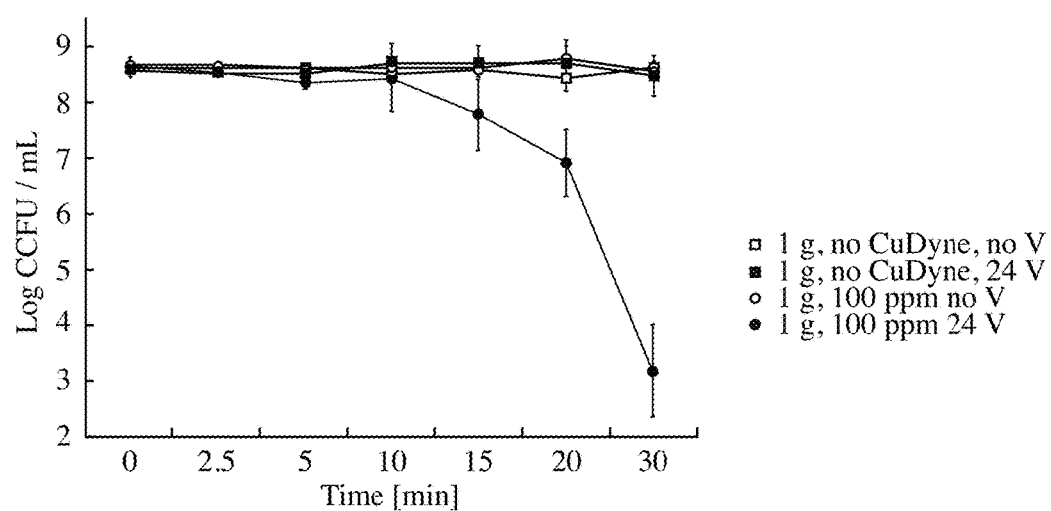
FIG. 2B is a graphic representation of ■1 g, no CuDyne, 24 V; ○1 g, 100 ppm, no V; ●1 g, 100 ppm, 24 V).

A cocktail of *S. enterica* was challenged in an EC batch cell containing expanded graphite (1 g) and Cupridyne® (100 ppm $I_2$), run at 24 V, to assess inactivation. Samples without graphite did not exhibit a reduction in numbers of *Salmonella* spp., with the exception of the sample containing 100 ppm $I_2$, run at 24 V, where an approximate 1-log reduction was observed at 30 min (FIG. 2*a*). Samples containing expanded graphite did not exhibit a reduction in *S. enterica*, with the exception of the sample containing 100 ppm $I_2$ run at 24 V (FIG. 2*b*); inactivation was observed to begin at 10 min, with an approximate 4-log reduction in numbers of *S. enterica* at 30 min (FIG. 2*b*). No differences were observed between plate counts obtained from VRBG and TSA (data not shown); plating on TSA was subsequently discontinued.

Samples run at 24 V exhibited ampere values between 0.4-1.0 A over the course of 30 min. Samples containing expanded graphite exhibited marginally higher amperage (data not shown). The pH values of all samples were observed to be 6 before treatment and did not change at the end of 30 min. Temperatures of all solutions prior to treatment were between 17-19° C. Samples run at 24 V exhibited a rise in temperature to between 31-41° C. at the end of 30 min.

3.2 Effect of Increased Levels of Cupridyne® Solution

Figure 3:
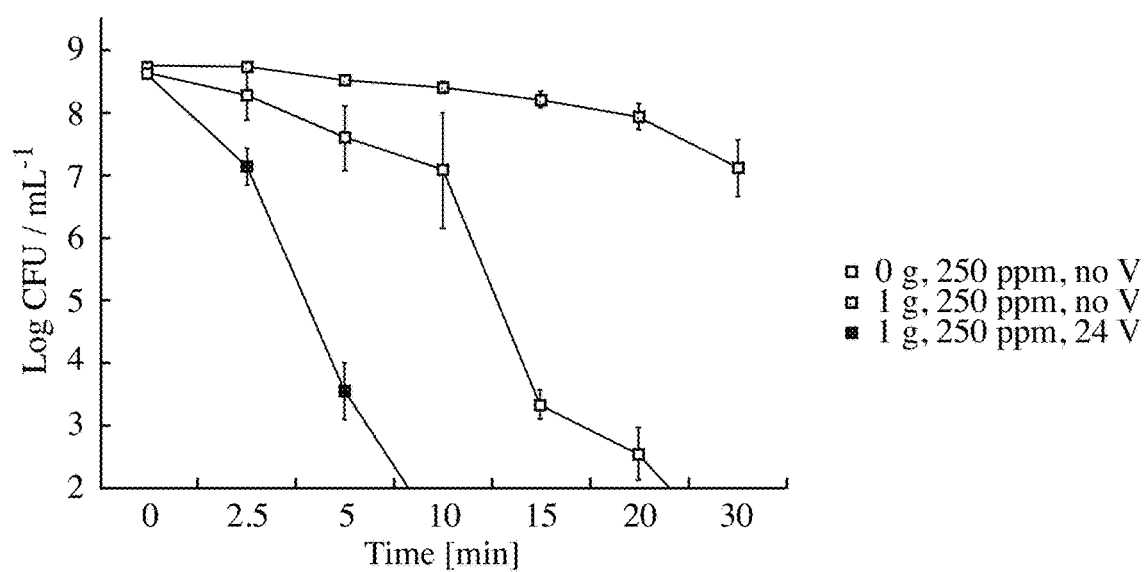
FIG. 3 is a graphic representation of Electrochemical treatment of *S. enterica* cocktail with 250 ppm Cupridyne® (□0 g, 250 ppm, no V; ✳1 g, 250 ppm, no V; ■1 g, 250 ppm, 24 V).

Cocktails of *S. enterica* were challenged in EC batch cells containing expanded graphite (1 g), either 250 ppm or 500 ppm Cupridyne®, at 24 V, to assess inactivation. Increased levels of Cupridyne® resulted in increased inactivation of *S. enterica* (FIG. 2). At 500 ppm, *Salmonella* spp. were inactivated below detection limit such that counts could not be obtained upon addition of Cupridyne® solution, regardless of the presence of graphite or voltage (data not shown). Populations of *S. enterica* were below detection limit after 5 min at 250 ppm (FIG. 3). Higher survival of *S. enterica* was observed in treatments where voltage was not applied (FIG. 3); however, Cupridyne® alone at 250 ppm achieved a greater inactivation of *S. enterica* relative to treatments where graphite and Cupridyne® were present in the absence of an applied voltage (FIG. 3).

3.3 Efficacy of KI in EC Batch Cell

Cocktails of *S. enterica* were challenged in EC batch cells containing expanded graphite (1 g), and potassium iodide (KI) or copper sulfate ($CuSO_4$), at 24 V, to assess individual Cupridyne® constituent effects on inactivation. The levels of KI and $CuSO_4$ used corresponded to equivalent amounts added together to make a 250 ppm Cupridyne® solution. The presence of copper sulfate did not inactivate *S. enterica* (FIG. 4). The presence of KI at levels equivalent to that in a 250 ppm solution of Cupridyne® solution inactivated the *S. enterica* cocktail population by >4 log CFU $mL^{-1}$ at 5 min, with levels falling below detection limit after 10 min (FIG. 4).

The efficacy of electrochemical (EC) disinfection systems that generate oxidants is attributed primarily to the generation of oxidation products at the anode. It should be noted that antimicrobial chemical species may also be generated at the cathode, typically through the reaction of oxygen ($O_2$) in water. No significant inactivation was observed in this study with regard to control trials lacking an iodine oxidant. Since reactive oxidant species generated at the cathode and anode are relatively short-lived, and no inactivation was observed in the absence of iodine, disinfection observed within this study is attributed primarily to the generation of reactive iodine species.

Studies that examine chlorine as a source of oxidants in an EC system tend to rely on resident levels of chloride ions instead of dosing a given system with additional chloride. Oxidation of resident chloride ions has become relatively popular in the application of electrolyzed water, pre-treated for subsequent use, as a disinfectant. Acid electrolyzed water is generated by passing a dilute salt solution (ex.: 1% NaCl) through an EC cell to generate chlorine oxidants. Acid electrolyzed water, often referred to as electrolyzed oxidizing water, has been shown to exhibit bactericidal activity against various microorganisms. Unfortunately, application of such electrolyzed water is problematic, given that its typical pH value (<2.7) facilitates chlorine off-gassing and can cause corrosion.

A crucial drawback to the use of prepared electrolyzed water as a disinfectant is the recorded dissipation of active oxidation products in solution within minutes of formation. As such, we opted to assess the efficacy of Cupridyne® and KI within a batch system to eliminate interference from dissipation effects. A mixture of graphite and iodine (Cupridyne® solution or KI) under applied voltage consistently inactivated *Salmonella* spp. in the presence of growth media (tryptic soy broth). Inactivation occurs rapidly in the presence of Cupridyne® solution, graphite, and an electric current, although continued exposure to Cupridyne® solution in the absence of graphite or an electric current also results in the inactivation of *S. enterica*. This effect scales with the amount of iodine added. It should be noted that increased inactivation was observed in the presence of Cupridyne® solution alone with no electric current, relative to Cupridyne® solution in the presence of graphite, likely due to adsorption effects of the graphite. It should also be noted that no appreciable inactivation of bacteria due to direct contact with electrodes was observed in control trials, likely due to the use of high numbers of microorganisms in spent growth media. The efficacy of KI solution under EC treatment was very similar to Cupridyne® solution, and is likely due to extensive oxidation of iodide to oxidants in both solutions.

As a disinfectant, Cupridyne® solution is effective over prolonged exposure.

Although $I_2$ will be formed via EC treatment, hypoiodous acid (HOI) is also thought to be a key antimicrobial iodine species, since HOCl and HOBr have been identified as antimicrobial species generated during EC disinfection. At the anode, where an acidic environment is established, iodate ($IO_3^-$) and possibly the iodine cation ($H_2OI^+$) will also act as antimicrobial oxidants/iodinating agents, although the concentration of the latter is contingent upon extremely low pH (pH<1). Overall, differentiation of killing effect provided by molecular iodine ($I_2$) and hypoiodous acid (HOI) in EC disinfection is unlikely, and both are likely contributors given the nature of the batch system used—oxidation and reduction at electrodes during constant mixing.

These examples support the use of iodine as an effective source of oxidants in EC disinfection. A high concentration of *S. enterica* was effectively inactivated (reduction of 7 log CFU $mL^{-1}$ in <10 min) in the presence of growth media (tryptic soy broth).

The present technology includes a method of filtering contaminants from a fluid stream by: providing a filter material comprising both carbon and (alkali halogen or alkaline halogen, such as alkali bromide, chloride, iodide or fluoride), e.g., potassium iodide, ambient halide within the contaminant-containing stream may also act to quickly or eventually activate the filter material if not already activated. Contaminant streams often contain halides, even up to 10, 25 100× a concentration amount sufficient to cause halide to migrate into the filter material (e.g., porous carbon) and activate the filter medium; passing a contaminated fluid stream in contact with the filter material; adsorbing contaminants from the fluid stream onto surfaces in the filter material; passing an electric current through the filter material with adsorbed contaminant thereon;

disassociating contaminant from the surfaces of the filter material; and removing disassociated contaminant from the filter material by carrying away the disassociated contaminant in a fluid flow mass.

The current causes the iodine to be emitted from the KI, and the iodine oxidizes the adsorbed pollutants/contaminants. Rather than a direct electrochemical oxidation that must be tailored for each pollutant, the present system allows a single voltage or current to release the iodine which can then address any pollutant. The carbon may be reactivated, regenerated by adding KI into the carbon, as by passing a solution through the filter material, causing adsorption of the KI molecules, with or without drying of the reactivating solution, or by voltage and current optimization to yield oxides instead of iodides as desired contaminant reaction products.

The filter material may be activated carbon and at least 0.05% by total weight of solids of potassium iodide. The potassium iodide may be intimately mixed throughout the activated carbon and/or the potassium iodide is distributed on at least some surfaces of the activated carbon. The electric current may be applied over a broad low to moderate range, such as being applied at voltages between 0.5 and 30V, preferably between 2.0 and 15 volts. The amperage may be as high as 6, or even 10 amps, and the minimum may be about 0.2 or 0.5 amps. The current may be applied after removal of the filter material from the contaminated fluid stream in a separate regenerative operational step. The fluid stream and the fluid flow mass may be a liquid stream and liquid flow mass, respectively.

The electric current may disassociate contaminant without irreversible reduction or irreversible oxidation of the contaminant.

Also described herein is an apparatus for removing contamination from a fluid stream having: a) a housing containing a filter material having two opposed surfaces, the filter material comprising carbon and an activating agent selected from the group consisting of an alkali metal halogen and an alkaline halogen; b) a fluid inlet port to the housing; c) a fluid outlet port from the housing; d) a source of contaminated fluid available to the fluid inlet port; e) a device for moving fluid through the inlet port and through the outlet port; f) a current source that passes current through the filter material between the two opposed surfaces; and g) a source of fluid flow mass to move fluid mass over the filter material after or during passage of direct current over the filter material.

The a) a housing contains a filter material, preferably comprising carbon and potassium iodide may be oriented to a pair of electrodes with flow moving from one electrode to the other (as cathode and anode, or anode to cathode) or between the two electrodes with current flow in one direction or the other perpendicular to the flow path;
  b) a fluid inlet port to the housing;
  c) a fluid outlet port from the housing;
  d) a source of contaminated fluid available to the fluid inlet port;
  e) a device for moving fluid through the inlet port and through the outlet port;
  f) a direct current source that passes direct current through the filter material; and
  g) a source of fluid flow mass to move fluid mass over the filter material after or during passage of direct current over the filter material.

Another aspect of technology described herein includes a liquid antimicrobial solution with: at least 80% of total weight of a carrier liquid comprising water, alcohol or a mixture of water and alcohol or other non-protic solvents; at least 0.001% by weight of the solution of $K^+I^-$; at least 0.001% by weight of $CuSO_4$; and sufficient acid in the solution to provide a pH of less than 5.0.

The solution may have acid in sufficient amount to provide a pH of from 2.0 to 4.8. The solution has a preferred acid of sulfamic acid.

In the present technology, a carbon filter is activated by intimate, internal association with iodine and/or potassium iodide (KI). This material will be referred to herein as IAC (for Iodine (iodide) activated carbon. Spent or used IAC has an aqueous or alcoholic liquid imbuing or flowing through the spent IAC while a current is passed through the spent IAC within the liquid. The current overcomes the forces binding adsorbed material to the IAC and regenerates the activity in the IAC while the liquid supports and is used to carry away the released formerly filtered and retained materials. As the adsorbed or absorbed materials filtered from either a gaseous or liquid medium are primarily associated with the activated carbon medium (the IAC) through electrical forces, as opposed to covalent bonding, application of current can be highly effective in freeing material bound to the IAC.

The adsorbed contaminants are released from adsorptive binding to the filters and then washed away. This can be done by removal and washing of the filtrate during application of the current, backflushing of the filter bed during application of the current, side flushing (at least one separate flowpath, e.g., a side path, other than the primary inlet and primary outlet paths of fluid flow through the filter bed), or other freed contaminant removal techniques. This system and technology can be used with both gaseous and liquid filtering systems, and can use gaseous removal systems where the freed contaminant is gaseous, or requires a fluid removal system (aqueous or organic or even inorganics such as mineral oil) depending upon the physical properties of the contaminant in its freed state and the available resources.

One aspect of the present technology is to first load the carbon filters with KI (which is being used as exemplary of all halide salts) because the carbon filter along with many other substances in nature possesses an "Iodine number"), e.g., with a water or alcohol solution of KI, and then (continuously) supply DC current across the filter while filtrate passes the assembly, to perform continuous oxidation of organics and metals by free iodine produced from the KI electrolysis described below:

$$I^- \rightarrow I._{sub.(aq)}I._{sub.2(s)} + 2e.^{sup.-}$$

$$2H_2O_{(l)} + 2e^- \rightarrow 2OH^-_{2(aq)} + H_{2(g)}$$

net reaction: $2I^-_{2(aq)} + 2H_2O_{(l)} \rightarrow I_22(s) + 2OH^-.(aq) + H_{2(g)}$ The filterable fluid then may be passed through the assembly of carbon filter plus electrolysis electrodes, where the free iodine oxidizes the target materials in the medium. This is done with, and without the addition of additional KI upstream. Experimental results produces an obvious layer of brown iodine/KI solution between the electrodes at a separation of 3" between carbon electrodes (in this case) as distinct from the remaining KI solution which remains clear (but contains KI) at nominal DC 6-30 v, 0.08 A. The current may be passed in various directions to modify results, even from causing oxidation with current flow in one direction and reduction with opposite direction fluid flow. The current may be across the liquid flow path (e.g., water or aqueous solution) between the electrodes in directions parallel with the liquid flow path, anti-parallel with the liquid flow path, perpendicular the liquid flow path (in one direction or another).

Similar to the above is the instance where the DC electrolysis energy is replaced by UVC (ultraviolet radiation concentration exposure), typically 253.9-266.0 nm (although within the range of 250-300 nm is particularly useful), but takes longer, and is subject to occlusion by glass and TDS or TSS in the filterable solution.

Gel with Iodine and Boron to Control Radiation Leaks

This aspect of the technology prescribes that the chemical basis of nuclear fuel control rods (boron from boric acid, hafnium, cadmium) be suspended in our CupriDyne-SAP™ gel to a desired consistency without breaking the gel, and then disposing on spent fuel rods, fuel rods, and other nuclear plant containment vessels and areas, to absorb neutrons, and cool down the target. This is useful when water cannot be used, but desirable also in that the flocculent of SAP will acquire the fission products as well, and prevent exposure to alpha, beta, and most gamma rays. Just as firefighting using fire retardant chemicals is dropped from the air, likewise a gel will adhere to all surfaces to cool down the spill or problem rods. In essence, it is a gelled version of a control rod which can be pumped by emergency pumpers. Water with boric acid has been tried by the Japanese, but the amount of boric acid is limited to 3-5%, especially in sea water—not enough to cool down the fuel rods, and then the water leaked out from containment in the particular instance, anyway.

Stable Iodine Liquid Compositions/Solutions (Ready to Use and Concentrate)

An iodine solution is acidified by the addition of an acid that (alone) produces a pH of less than 6.7 at 1.0 N in deionized water and preferably less than 6.5 under those parameters. Typical acids may be organic acids, inorganic acids, Lewis acids, HCl, HI, HBr (halogenic acids), $HNO_3$, $HClO_4$, $H_2SO_4$, $H_2SO_3$, and especially the family of sulfamic acids.

The iodine environment can be provided in numerous and varied tasks and services and even in combination with other additives such as stable active solutions or film-breaking compositions such as acids (e.g., sulfamic acid, hydrochloric acid, sulfuric acid, enzymes, etc.). At present, the most widely known and accepted acidizing agents include HCl, sulfamic acid, lactic acid, citric acid, and acetic acid, all with varying degrees of reactivity for descaling. The effect of acidizing with iodine gas in solution, however, also attends with additive antimicrobial effects, and when the acidized iodine is combined with sulfamic acid, a powerful and effective method is provided for dissolving and remediating biofilms, and chelating heavy metals which may be solubilized by the process, or otherwise contained in water, especially after physical disruption as described herein.

Sulfamic acid is also a primitive surfactant, and when added to free iodine in water and stabilized by varying added compounds such as silicates (e.g., sodium metasilicate) and phosphates and sulfonates (e.g., sodium xylene sulfonate or phosphate), yields a disinfecting and biofilm removing detergent compound which is active within the technologies described herein for oilfield or watershed applications as a single formulary product. The term a "sulfamic acid compound" or a member of the family of sulfamic acids or class of sulfamic acids is herein defined as any sulfamic acid central moiety with a single substituent on the amide group of the sulfamic acid moiety or sulfamic acid core structure that still allows the sulfamic acid derivative in the family of sulfamic acids to display a pH of less than 6.8 at 0.5N in deionized water, preferably less than 6.5 under those parameters (e.g., 5.5 to 6.7, 5.5 to 6.2, and 4.0-6.7, and 3.0 to 6.7 and even lower levels of acidity up to 6.5, up to 6.6 or up to 6.7 pH). As non-limiting examples of these known sulfamic acid family compounds are sulfamic acid, iodosulfamic acid, chlorosulfamic acid, bromosulfamic acid, fluorosulfamic acid, alkylsulfamic acid (with C1-C8 carbon groups, whether linear, branched or cyclic, such as cycloheylsulfamic acid, and substituted or not, such as trifluoromethylsulfamic acid, pentachloroethylsulfamic acid, etc.), cyanosulfamic acid, any electron-withdrawing group on the amide position of the sulfamic acid and even lightly electron-donating groups that do not change the sulfamic acid from an acid to a base at 1.0N in deionized water.

The formula for sulfamic acid is $NH_2SO_3H$ and the corresponding formula for a sulfamic acid compound is represented by:

$NR_2SO_3H$, wherein R is independently selected from the groups described above, such as hydrogen, halogen, cyano, C1-C6 alkyl or substituted alkyl, perhalo alkyl, halosubstituted alkyl, electron-withdrawing groups, mild electron-donating groups and the like. It is preferred that at least one R group is hydrogen.

The inventor has noted that the addition of sulfamic acid (in particular) to all CupriDyne™ treatment composition formulas can provide ultimate stability or even enhanced activity in its various antimicrobial or surface treatment procedures. The sulfamic acid is both an acidifying agent (and other acids may be used) and a primitive surfactant. CupriDyne™ antimicrobial compositions in water is stabilized (free iodine is continuously available) by lowering pH to 5.5-6.7. Even the CuI resulting component is held in solution. The addition of surfactants, such as sodium metasilicate and sodium tripolyphosphate assists in completing a detergent preparation formula. The solutions may have normal levels of iodine therein (e.g., at least 5 ppm or may be concentrated for dilution with greater than 50 ppm, greater than 100 ppm, greater than 200 ppm, up to solubility limits of iodine in aqueous or alcohol solvents.

The solution is preferred where the acid comprises a sulfamic acid compound having the formula:

$NR_2SO_3H$, wherein R is independently selected from the group consisting of hydrogen and electron-withdrawing groups. The acid may comprise a sulfamic acid compound having the formula:

$NR_2SO_3H$, wherein R is independently selected from the group consisting of hydrogen, halogen, cyano, C1-C6 alkyl, C1 to C6 substituted alkyl, perhalo alkyl, halosubstituted alkyl, and electron-withdrawing groups.

The solution may have at least one R is hydrogen in the sulfamic acid compound or only and exactly one R is hydrogen.

These solutions are antimicrobial, have anti-odor effects, and can bleach or remove some stains. The solutions may be applied by direct application of the liquid as a wash, spray, wipe, mist, bath, or provided in a delivery system. The delivery system may be a diffusion, infusion, frangible, desorption, exudation, or other systems. Solid media such as porous foam, slowly soluble solid medium (e.g., alcohol soluble medium carrying dispersed water droplets), thermally openable media (media with pores that may be further opened or expanded to increase outward flow or diffusion of actives, e.g., small pore solid, where pore size increases with heat), a solid composition having soluble solids dispersed therein that can be dissolved o open pores (e.g., NaCl dispersed in polyamide, polyvinylalcohol dispersed in polyolefin, etc.), and the like. Pastes containing high concentrations of the liquid (e.g., cornstarch, PVA, polyvinylpyrrolidone, cellulose bases, clay bases, putty, and the like) can be applied to surfaces. Greases or sealants can be applied at joints, seals, areas susceptible to leakage, or placed within environments that may be stable before operating events and need to be activated under use conditions. Simple wettable carriers such as wood chips, saw dust, cellulose fibers, superabsorbent polymers, fabrics, dissolvable pouches, and the like may be positioned within areas where subsequent materials with contaminants are likely to be added during use. The liquid will then be active against microbes and odors and other contaminants.

Example target applications are waste disposal containers, for industrial, medical, residential and commercial fields of utility. Colostomy bags, catheterization collection areas, medical waste disposal boxes or tins, trash cans, garbage cans, bins, containers, litter boxes, and stall bedding are other possible applications. Any tubing or transport carriers may also be treated according to the present technology, by coatings, laminates, flushing, and the like.

The activated carbon may be maintained over an extended period of time by regeneration or partial regeneration of the Iodine Activated Carbon (iodine is used as an example, with each halogen atom or halide ion equivalent being contemplated). The contaminants (or materials to be purified) are removed from the fluid medium by the iodine chemically binding, forming a salt with or otherwise temporarily associating with those contaminants. Once a level of contaminant is bound to the IAC (either approaching the end of a batch, diminishing returns on the absorption capability of the IAC, saturation or near saturation of the IAC, a commercially useful level of bound material that is to be collected, and the like), the filtration process is halted. The medium flowing through the IAC bedding or column is then changed to a cleaner medium, such as water, alcohol, light organic liquids and/or mixtures thereof. Current, preferably direct current is passed through the loaded IAC while the fresh, clean medium is maintained in a batch operation or in a continuous operation. The applied current is varied by considering the relative strengths of the I-contaminant bond strength, the I-carbon bond strength, density of contaminants in the IAC, concentration of the dissociated contaminant in the fluid medium, flow rate of the medium across the loaded IAC and the like. For example, with a low I-contaminant bond strength and relatively higher I-carbon bond strength, low to intermediate currents (especially with sequences of cells in parallel or series connection) may be used in a batch or continuous process. As the difference in relative bond strengths narrows, higher currents are desirable, along with slower medium flow over the loaded IAC. Although DC (direct current) is clearly preferred, the use of alternating current (AC) produces measurable benefits and could be used in environments where AC is available.

FIG. 1 shows a schematic of a filter system 10 of the present invention with a power source 12 having a cathode 14 and an anode 18 attached to the filter material 16, with an expanded view 20 of the carbon in the filter 10.

Other variations within the generic scope of the invention can be designed by users to marginally improve or optimize the performance of the present invention and remain within the scope of the claims. Variations in concentrations, flow rates, volumes, current and other controllable parameters are within the skill of the ordinary artisan.

What is claimed:

1. A method of generating reductive and/or oxidative chemical species in an aqueous fluid stream to disinfect and/or remove contamination comprising:
   a) providing a filter material comprising at least two filter elements comprising at least one porous carbon support layer and a silicate wool or glass wool layer in direct contact with the at least one porous carbon support layer;
   b) passing an electric current through the at least two filter elements;
   c) passing a fluid stream containing elemental halogens and/or halide salts through the at least two filter elements, thereby distributing halogens or halides within the at least two filter elements;
   d) subsequent to distributing halogens or halides within the at least two filter elements directing a contaminated fluid mass into contact with the at least two filter elements in the presence of the electric current; and
   e) adsorbing contaminants from the fluid mass onto the at least two filter elements, thereby disinfecting or removing the contaminants;
   wherein the electric current flows in a direction perpendicular to movement of the fluid stream.

2. The method of claim 1 wherein the at least two filter elements are divided into discrete sections of at least two sections, each of the discrete sections having a spacer element in direct contact with adjacent filter elements and the filter elements disinfect microbes, and wherein absorbed contaminant is disassociated from surfaces of the at least two filter elements and disassociated contaminant is removed from the filter material by carrying away the disassociated contaminant in the fluid flow mass.

3. The method of claim 2 wherein the spacer element consists essentially of a silicate wool spacer.

4. The method of claim 1 wherein the filter material comprises activated carbon and from 0.01% to 80.00% by total weight of solids silicate wool or glass wool as the silicate wool or glass wool layer, the filter material produced by packing and shaping of the filter material in dry state or when saturated in an aqueous or alcohol solution.

5. The method of claim 1 wherein the fluid stream contains halide salts comprising hydrogen halide and/or potassium halide, and/or sodium halide, and/or calcium di-halide.

6. The method of claim 1 wherein the electric current is applied at voltages between 0.05 and 36 volts.

7. The method of claim 6 wherein the electric current is applied before and during passing a contaminated fluid through the filter material.

8. The method of claim 1 wherein the fluid stream comprises water and elemental Iodine.

9. The method of claim 8 wherein the fluid stream further comprises ionic species of iodine, copper, potassium and sulfate.

10. The method of claim 1 wherein c) is performed at the same time that b) is initiated.

11. The method of claim 1 wherein the method is performed on an apparatus for disinfecting and/or removing contamination from a fluid comprising:
   f) a housing containing the at least two-filter elements;
   g) a spacer material between the at least two filter elements, in contact with adjacent filter elements, to separate the at least two filter elements into discrete sections;
   h) a fluid inlet port to the housing;
   i) a fluid outlet port from the housing corresponding to each discrete section of the filter material as separated by the spacer material;
   j) a source of contaminated fluid mass available to the fluid inlet port;
   k) a source of halide salts or elemental halogen in an aqueous carrier available for movement into the at least two filter elements;
   l) a source of pressure for moving active fluid selected from the group consisting of the contaminated fluid mass and the halide salts or elemental halogen in an aqueous carrier through the inlet port and through the outlet port;

m) a current source configured to pass a voltage of between 0.05 and 36 volts across the at least two filter elements; and n) a source of fluid flow mass to move fluid mass through the filter material during passage of direct current through the at least two filter elements.

12. The method of claim 3 wherein the at least two filter elements comprise activated carbon and from 0.01% to 80.00% by total weight of solids silicate wool or glass wool, the at least two filter elements produced by packing and shaping of the activated carbon in a dry state or when saturated in an aqueous or alcohol solution.

13. The method of claim 11 wherein the fluid stream contains halide salts comprising hydrogen halide, and/or potassium halide, and/or sodium halide, and/or calcium di-halide, and wherein absorbed contaminant is disassociated from surfaces of the at least two filter elements and disassociated contaminant is removed from the filter material by carrying away the disassociated contaminant in the fluid flow mass.

14. The method of claim 1 wherein the electric current is applied at voltages between 0.05 and 36 volts.

15. The method of claim 14 wherein the electric current is applied before and during passing a contaminated fluid through the at least two filter elements.

16. The method of claim 1 wherein the fluid stream comprises water and elemental Iodine.

17. The method of claim 1 wherein c) is performed before or at the same time that b) is initiated, or wherein b) is initiated before c).

* * * * *